United States Patent
Turner et al.

(10) Patent No.: US 8,708,991 B2
(45) Date of Patent: Apr. 29, 2014

(54) TOURNIQUET WITH DISPOSABLE ABSORBENT ELEMENT

(75) Inventors: Jason Turner, Rockwood (CA); Mario Lopez, Courtice (CA)

(73) Assignee: 2301142 Ontario Inc., Rockwood, Ontario (CA)

( * ) Notice: Subject to any disclaimer, the term of this patent is extended or adjusted under 35 U.S.C. 154(b) by 371 days.

(21) Appl. No.: 12/986,987

(22) Filed: Jan. 7, 2011

(65) Prior Publication Data

US 2012/0089109 A1  Apr. 12, 2012

Related U.S. Application Data

(60) Provisional application No. 61/390,660, filed on Oct. 7, 2010.

(51) Int. Cl.
*A61F 13/15* (2006.01)

(52) U.S. Cl.
USPC ........... 604/392; 604/358; 604/543; 604/308; 606/203; 602/43

(58) Field of Classification Search
USPC ................. 604/304, 307–308, 358, 385.01, 604/386–387, 391–393; 606/203, 185
See application file for complete search history.

(56) References Cited

U.S. PATENT DOCUMENTS

| | | | |
|---|---|---|---|
| 2,113,534 A * | 4/1938 | Brown | 606/203 |
| 2,936,759 A | 5/1960 | Yuhas | |
| 3,050,064 A | 8/1962 | Moore et al. | |
| D217,186 S | 4/1970 | Smith | |
| 3,586,001 A * | 6/1971 | Sanderson | 606/203 |
| 3,782,378 A * | 1/1974 | Page | 128/888 |
| 4,182,338 A | 1/1980 | Stanulis | |
| 4,997,438 A | 3/1991 | Nipper | |
| 5,070,886 A * | 12/1991 | Mitchen et al. | 600/584 |
| 5,263,965 A | 11/1993 | Roth | |
| 5,269,803 A | 12/1993 | Geary et al. | |
| 5,411,518 A * | 5/1995 | Goldstein et al. | 606/202 |
| 5,499,966 A * | 3/1996 | Bulley et al. | 602/42 |
| 5,512,056 A | 4/1996 | Stevens et al. | |
| 5,695,520 A | 12/1997 | Bruckner et al. | |
| 6,189,538 B1 | 2/2001 | Thorpe | |
| 7,326,227 B2 * | 2/2008 | Dedo et al. | 606/203 |
| 7,943,810 B2 * | 5/2011 | Buckman et al. | 602/48 |
| 8,343,074 B2 * | 1/2013 | Weidenhaupt et al. | 600/583 |
| 2004/0092999 A1 * | 5/2004 | Lojewski | 606/185 |
| 2004/0243044 A1 * | 12/2004 | Penegor et al. | 602/48 |
| 2005/0267518 A1 * | 12/2005 | Wright et al. | 606/203 |
| 2006/0079823 A1 * | 4/2006 | Utterberg et al. | 602/53 |
| 2009/0198152 A1 * | 8/2009 | Kim | 600/583 |
| 2012/0150215 A1 * | 6/2012 | Donald | 606/203 |

* cited by examiner

*Primary Examiner* — Michele M Kidwell
(74) *Attorney, Agent, or Firm* — Taylor English Duma LLP

(57) ABSTRACT

Disclosed is an apparatus for use when a hypodermic needle, partially protruding from a limb, is to be withdrawn fully from the limb to leave a puncture wound. The apparatus comprises an absorber, a receiver and, optionally, a strap. The absorber includes a medium which is able to absorb blood. In use, the absorber is placed in overlying, abutting relation to the needle prior to withdrawal of the needle from the limb. Following withdrawal of the needle from the limb, absorber is urged against the puncture wound to promote hemostasis. The receiver in use, is releasably connected to the absorber. The strap can be coupled to the receiver to define, in use and in combination with the apparatus, a tourniquet. The absorber can be disposable and the strap and receiver can be reusable.

12 Claims, 7 Drawing Sheets

TOURNIQUET WITH DISPOSABLE ABSORBENT ELEMENT

This application claims priority to U.S. Provisional Patent Application No. 61/390,660 filed Oct. 7, 2010, incorporated herein by reference in its entirety.

FIELD OF THE INVENTION

The present invention relates to medical apparatuses for promoting haemostasis and absorbing blood discharged from a wound, and more particularly to a medical apparatus for use with a hypodermic needle.

BACKGROUND OF THE INVENTION

It is commonplace to use hypodermic needles in medical treatment and it is well known that some bleeding will usually follow needle withdrawal. In most cases, this is not problematic, as haemostasis will occur relatively quickly. In the case of a haemophiliac, however, haemostasis is compromised. Thus, a haemophiliac is generally in need of an apparatus for promoting haemostasis following use of a hypodermic needle.

SUMMARY OF THE INVENTION

In accordance with one aspect of the invention, there is disclosed an apparatus for use when a hypodermic needle, partially protruding from a limb, is to be withdrawn fully from the limb to leave a puncture wound. This apparatus comprises an absorber and a receiver. The absorber includes a medium which is able to absorb blood. The absorber, in use, is placed in overlying, abutting relation to the needle prior to withdrawal of the needle from the limb and, following withdrawal of the needle from the limb, is urged against the puncture wound to promote haemostasis. The receiver is releasably connected to the absorber.

In accordance with another aspect of the invention, the absorber and receiver can be provided with a quick release adaptation such that, after use, the absorber can be released by hand without exposure to the medium.

In accordance with yet another aspect of the invention, the receiver can define a socket which presents toward the puncture wound in use and the absorber can be disposed within the socket in use.

In accordance with yet another aspect of the invention, the absorber and receiver can be adapted such that, following use, and upon application of a release force between the absorber and receiver, the connection between the absorber and the receiver can be released. The receiver can define an aperture which communicates with the socket. The aperture can be sized and positioned to permit a digit of said hand to pass through the aperture and apply the release force to the absorber thereby to provide the quick release adaptation.

In accordance with yet another aspect of the invention, upon disposition of the absorber in the socket, the receiver and absorber can engage one another in snap-fit relation to provide for the releasable connection between the receiver and absorber.

In accordance with yet another aspect of the invention, the absorber can be provided with a pressure relief adaptation sufficient to avoid material interference with the needle when the absorber is in said overlying, abutting relation.

In accordance with yet another aspect of the invention, the absorber can comprise a housing in the form of a bowl and the bowl can contain the medium and have a sidewall.

In accordance with yet another aspect of the invention, the pressure relief adaptation can be defined by a cut-out in said sidewall which defines a passage through which said needle passes when the absorber is in overlying, abutting relation.

In accordance with yet another aspect of the invention, the apparatus can further comprise a strap coupled to the receiver to define, in use and in combination with the apparatus, a tourniquet.

In accordance with yet another aspect of the invention, the receiver can have a pair of opposed lugs and the strap can be coupled to the receiver in the manner by which a watch band is coupled to a timepiece to form a wrist watch.

In accordance with yet another aspect of the invention, the absorber can be disposable and the strap and receiver can be reusable.

Forming another aspect of the invention is an apparatus, for use when a hypodermic needle, partially protruding from a limb, is to be withdrawn fully from the limb to leave a puncture wound. This apparatus comprises a bowl and a medium. The medium is able to absorb blood and is disposed in the bowl to define, in combination therewith, an absorber. The absorber, in use, is placed in overlying, abutting relation to the needle prior to withdrawal of the needle from the limb and, following withdrawal of the needle from the limb, is urged against the puncture wound to promote haemostasis.

By placing the absorption medium in overlying, abutting relation to the needle insertion site, the present invention limits the exposure of the wound to the outside environment. This accordingly reduces the risk of infection. Moreover, by releasably connecting the receiver to the absorber, the present invention allows the soiled absorption medium to be disposed of following use without requiring handling of the absorption medium which has advantages in terms of sanitation and consumer acceptance.

Other advantages, features and characteristics of the invention, as well as method of operation and functions of the related elements of the structure, and the combination of parts and economies of manufacture, will become more apparent upon consideration of the following detailed description and the appended claims with reference to the accompanying drawings, the latter being briefly described herein below.

DETAILED DESCRIPTION

Figure 1:
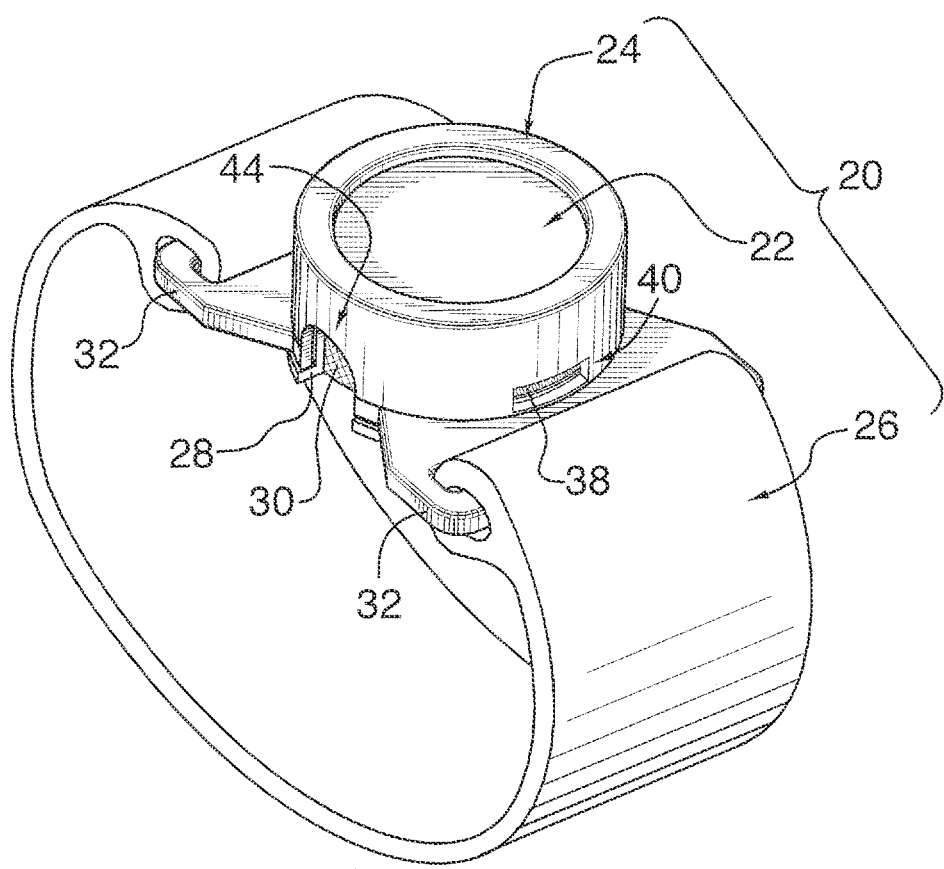
FIG. 1 is a perspective view of an exemplary embodiment of the apparatus.

An exemplary embodiment of the invention is illustrated in FIG. 1 and designated with general reference numeral 20. The apparatus 20 will be seen to comprise an absorber 22, a receiver 24 and a strap 26.

Figure 3:
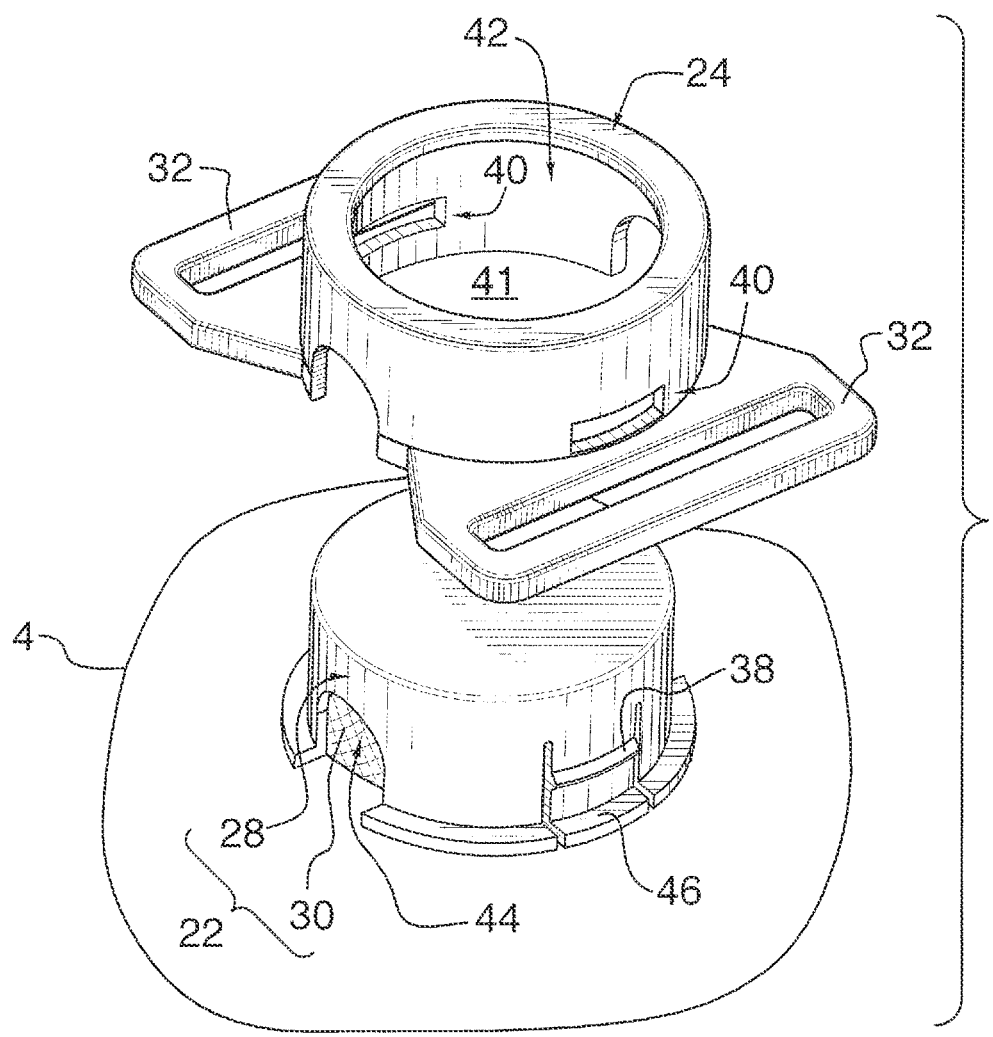
FIG. 3 is an exploded view of the structure of FIG. 2.
Figure 4:
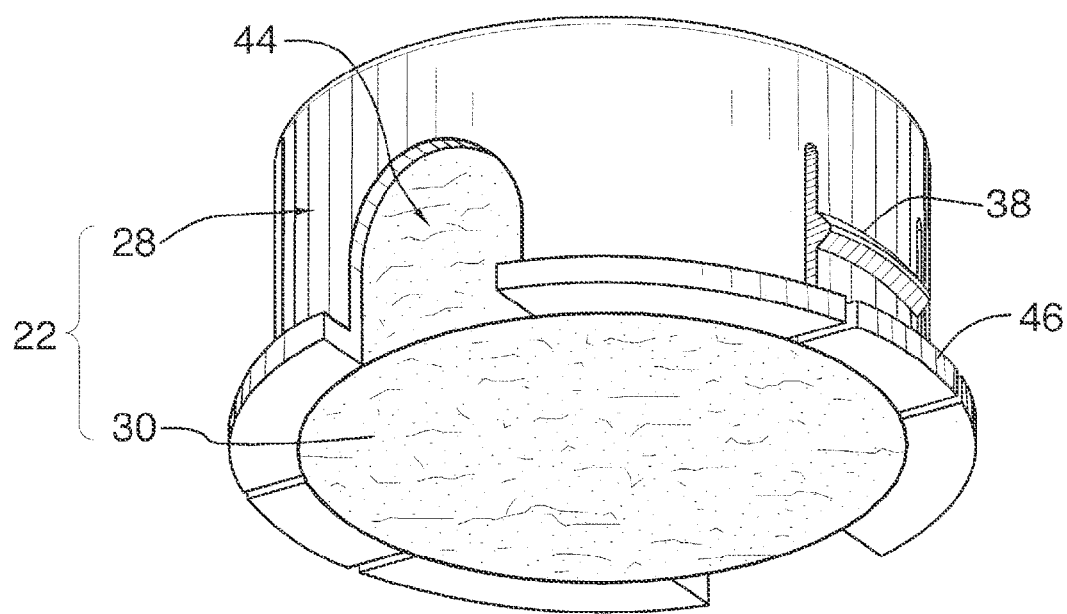
FIG. 4 is a view of encircled structure 4 of FIG. 3, from another vantage point.

With reference to FIG. 3, the absorber 22 will be seen comprise a bowl-shaped housing 28 and a medium 30. The housing 28 has a side-wall with a cut-out 44 defined therein. The housing 28 further includes a pair of flexible tabs 46 which each have a projection 38 formed thereon. The medium 30 is a compressible gauze pad.

The receiver 24 will be seen to define a socket 41, have an aperture 42 in communication with the socket 41, a pair of opposed lugs 32 and a pair of slots 40. The aperture 42 is sized and positioned such that a digit of a hand can be fitted therethrough.

Returning to FIG. 1, the strap 26 will be seen to be coupled to the lugs 32 of the receiver 24 in a manner by which a watch band is coupled to a timepiece to form a wrist watch.

When operatively configured, as shown in FIG. 1, the absorber 22 occupies the socket 41 (not identified) of the receiver 24. Once the absorber 22 is fully seated in the socket 41, projections 38 engage slots 40, to releasably connect absorber 22 to receiver 24 in snap-fit relation. It will be noted that, in this operative configuration, the aperture 42 exposes the absorber 22, more particularly, the housing 28.

Figure 1A:
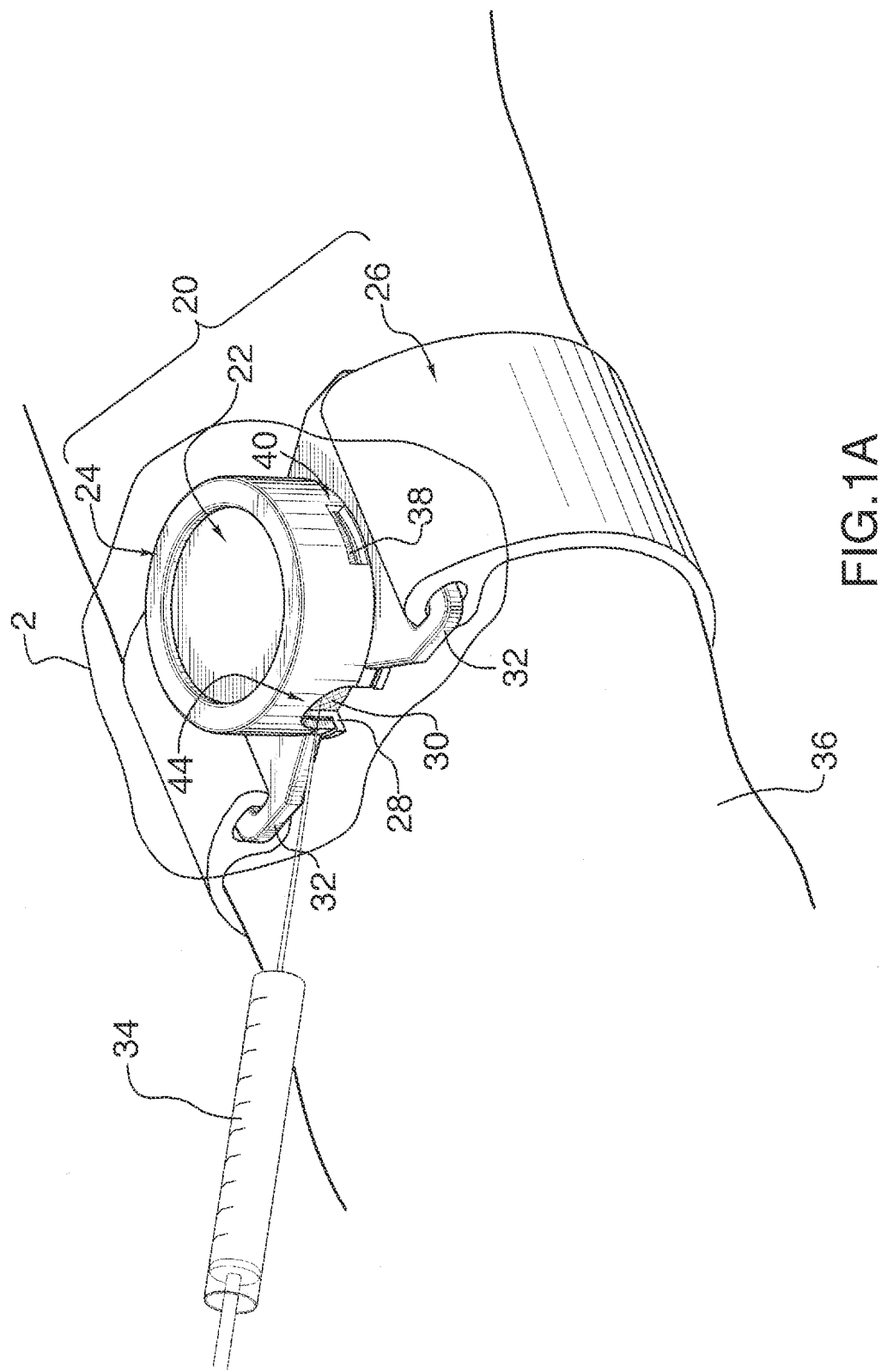
FIG. 1A is a perspective view of the structure of FIG. 1 in use.
Figure 2:
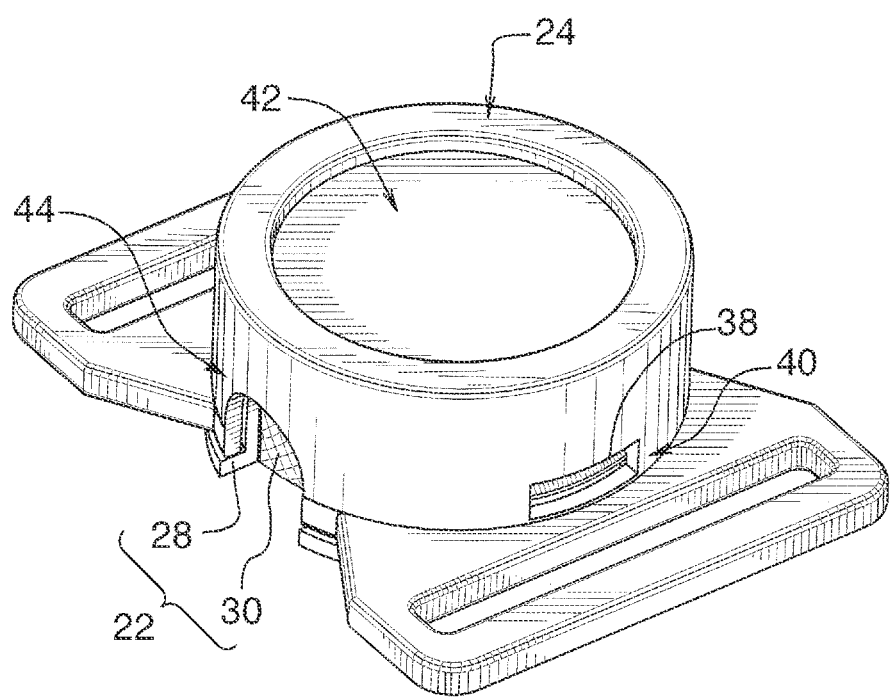
FIG. 2 is an enlarged view of encircled area 2 of FIG. 1A.

The apparatus 20 is depicted in use in FIG. 1A. Herein, a limb 36, namely, an arm of a user is shown, a hypodermic needle 34 is seen partially protruding from the limb 36 and the apparatus 20 is seen to be in overlying, abutting relation to the insertion site of the hypodermic needle 34. The cut-out 44 provides a passage through which the hypodermic needle 34 passes and the compressible nature of the medium 30 is such that, as so positioned, the apparatus 20 does not materially interfere with the hypodermic needle 34, i.e. stress the wound, yet, as the hypodermic needle 34 is withdrawn from the limb 36, the absorber 22 can absorb any blood that discharges from the wound.

Figure 6:
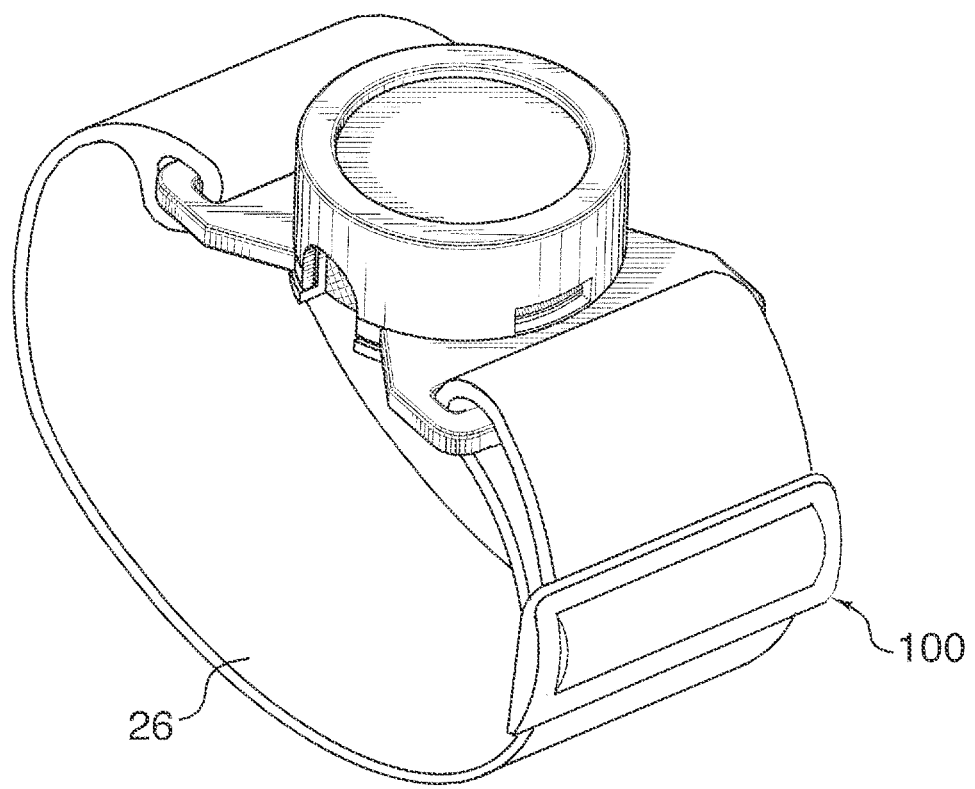
FIG. 6 is a view similar to FIG. 1 showing another exemplary embodiment of the apparatus.

When the hypodermic needle 34 has been completely withdrawn from the limb 36, the strap 26 can be tightened to pressurize the absorber 22 against the wound and promote haemostasis, i.e. the strap 26 provides tension which holds the absorber 22 and the receiver 24 in position. It should be understood that although means of strap-tightening are not illustrated in FIG. 1, being well-known to persons of skill in the art, a number of means of strap-tightening can be easily and readily implemented in the present invention and all are contemplated. FIG. 6, for example, shows an embodiment wherein the strap 26 includes a buckle 100 to permit strap tightening.

Figure 5:
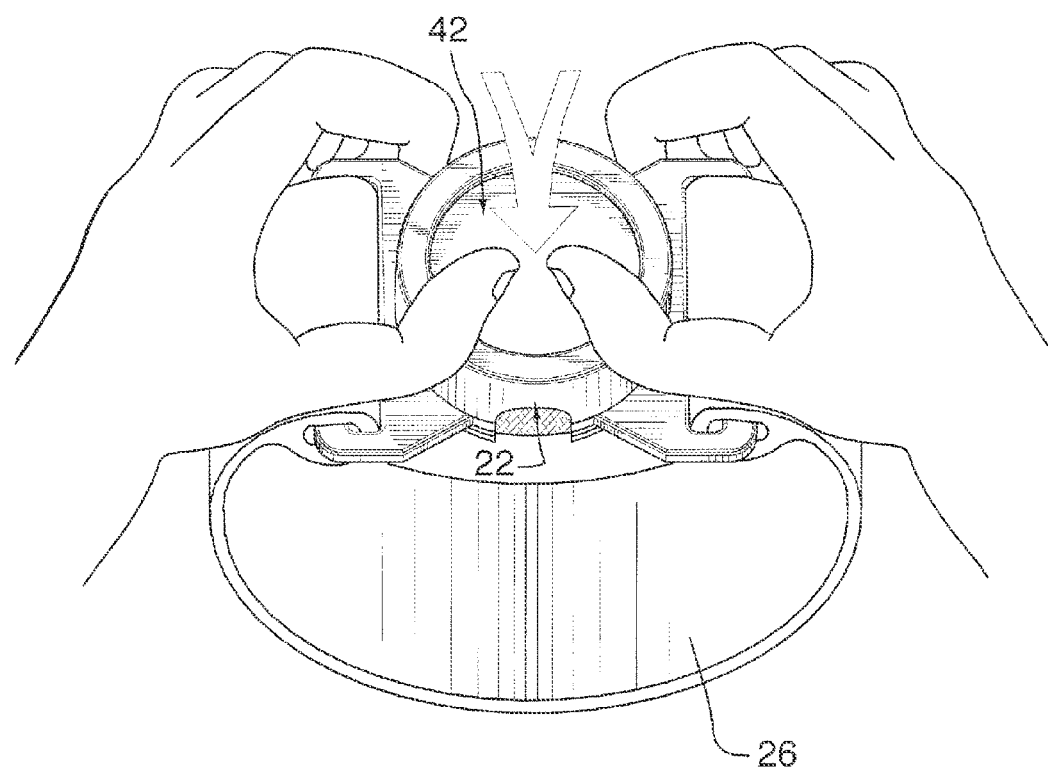
FIG. 5 is a view of the structure of FIG. 1, showing a user applying a release force to the absorber.

Once haemostasis has been attained, the apparatus can be removed from limb 36 and the user can force a digit of his or her hand, i.e. a thumb, through aperture 42 to apply a release force to the absorber 22, as shown in FIG. 5. This will cause the flexible tabs 46 (not shown in FIG. 5) to deflect, to allow the absorber 22 to be ejected from the socket 41 and into, for example, a garbage receptacle. Tabs 46 and slots 40 will thus be understood to define a quick release adaptation. In applying the release force, the thumbs will only come in contact with housing 28 of the absorber 22, that is, the thumbs will not come into contact with the soiled medium 30.

With the soiled absorber now discarded, a new absorber can be inserted before the next use of the apparatus.

Routine changes in the size, shape and configuration of the receiver and absorber can be made without affecting the functioning of the invention.

For example, the medium could be a cotton pad or some other type of absorption medium.

As well, the housing could, for example, be formed in a unitary fashion with the medium.

Further, although the absorber is depicted as engaging the receiver in a particular snap-fit relation, other snap-fit and quick-release mechanisms can be utilized.

Accordingly, it will be understood that the invention is limited only by the claims appended hereto, purposively construed. Thus, the above references to the "invention" should be understood to apply only to the disclosed embodiments, which are merely examples, among others, included within the scope of the appended claims.

The invention claimed is:

1. Apparatus for use when a hypodermic needle, partially protruding from a limb, is to be withdrawn fully from the limb to leave a puncture wound, the apparatus comprising:
   an absorber including a medium which is able to absorb blood, the absorber, in use
      being placed in overlying, abutting relation to the needle prior to withdrawal of the needle from the limb; and
      following withdrawal of the needle from the limb, being urged against the puncture wound to promote hemostasis; and
   a receiver which, in use, is releasably connected to the absorber and wherein the absorber and receiver are adapted such that, following use, and upon application of a release force between the absorber and receiver, the connection between the absorber and receiver is released.

2. Apparatus according to claim 1, wherein the absorber and receiver are provided with a quick release adaptation such that, after use, the absorber can be released by hand without exposure to the medium.

3. Apparatus according to claim 2, wherein
   the receiver defines a socket which presents toward the puncture wound in use; and
   the absorber is disposed within the socket in use.

4. Apparatus according to claim 3, wherein:
   the receiver defines an aperture which communicates with the socket, the aperture being sized and positioned to permit a digit of said hand to pass through the aperture and apply said release force to the absorber,
   thereby to provide said quick release adaptation.

5. Apparatus according to claim 4, wherein, upon disposition of the absorber in the socket, the receiver and absorber engage one another in snap-fit relation to provide for said releasable connection between the receiver and absorber.

6. Apparatus according to claim 3, wherein the absorber is provided with a pressure relief adaptation sufficient to avoid material interference with the needle when the absorber is in said overlying, abutting relation.

7. Apparatus according to claim 6, wherein the absorber comprises a housing in the form of a bowl, the bowl containing the medium and having a sidewall.

8. Apparatus according to claim 7, wherein said pressure relief adaptation is defined by a cut-out in said sidewall which defines a passage through which said needle passes when the absorber is in said overlying, abutting relation.

9. Apparatus according to claim 1, further comprising:
   a strap coupled to the receiver to define, in use and in combination with the apparatus, a tourniquet.

10. Apparatus according to claim 9, wherein the receiver has a pair of opposed lugs and the strap is coupled to the receiver in the manner by which a watch band is coupled to a timepiece to form a wrist watch.

11. Apparatus according to claim 9, wherein the absorber is disposable and the strap and receiver are reusable.

12. Apparatus for use when a hypodermic needle, partially protruding from a limb, is to be withdrawn fully from the limb to leave a puncture wound, the apparatus comprising:
   a bowl;
   a medium which is able to absorb blood and which is disposed in the bowl to define, in combination therewith, an absorber, the absorber, in use
      being placed in overlying, abutting relation to the needle prior to withdrawal of the needle from the limb; and following withdrawal of the needle from the limb, being urged against the puncture wound to promote haemostasis; and a receiver which, in use, is releasably connected to the absorber, the receiver sized to accept the bowl.

* * * * *